(12) United States Patent
Sarkar et al.

(10) Patent No.: US 11,352,661 B2
(45) Date of Patent: Jun. 7, 2022

(54) SINGLE CELL FLUORESCENCE IN SITU HYBRIDIZATION IN MICROFLUIDIC DROPLETS

(71) Applicant: Northeastern University, Boston, MA (US)

(72) Inventors: Saheli Sarkar, Boston, MA (US); Tania Konry, Boston, MA (US)

(73) Assignee: Northeastern University, Boston, MA (US)

( * ) Notice: Subject to any disclaimer, the term of this patent is extended or adjusted under 35 U.S.C. 154(b) by 628 days.

(21) Appl. No.: 16/317,308

(22) PCT Filed: Jul. 12, 2017

(86) PCT No.: PCT/US2017/041775
§ 371 (c)(1),
(2) Date: Jan. 11, 2019

(87) PCT Pub. No.: WO2018/013726
PCT Pub. Date: Jan. 18, 2018

(65) Prior Publication Data
US 2021/0277455 A1      Sep. 9, 2021

Related U.S. Application Data

(60) Provisional application No. 62/361,035, filed on Jul. 12, 2016.

(51) Int. Cl.
*C12Q 1/6841* (2018.01)
*B01L 3/00* (2006.01)
*G01N 21/64* (2006.01)

(52) U.S. Cl.
CPC ...... *C12Q 1/6841* (2013.01); *B01L 3/502784* (2013.01); *G01N 21/6458* (2013.01);
(Continued)

(58) Field of Classification Search
CPC .............. C12Q 1/6841; G01N 21/6458; B01L 3/502784; B01L 2400/0487;
(Continued)

(56) References Cited

U.S. PATENT DOCUMENTS

2006/0063160 A1   3/2006   West et al.
2010/0070191 A1   3/2010   Gold et al.
(Continued)

FOREIGN PATENT DOCUMENTS

WO   2008130623 A1   10/2008
WO   2009011808 A1   1/2009
(Continued)

OTHER PUBLICATIONS

Droplet-based microfluidic system for multicellular tumor spheroid formation and anticancer drug testing† Linfen Yu,a Michael C. W. Chena and Karen C. Cheung*a Lab Chip, 2010,10, 2424-2432 https://doi.org/10.1039/C004590J First published Aug. 6, 2010 (Year: 2010).*

(Continued)

*Primary Examiner* — Jennifer Wecker
*Assistant Examiner* — Jonathan Bortoli
(74) *Attorney, Agent, or Firm* — Verrill Dana, LLP

(57) ABSTRACT

The invention provides a device, method, and system for high throughput detection of nucleic acid expression in individual cells. Cells are encapsulated in aqueous microdroplets which are merged with a biocompatible matrix, allowing on-chip fluorescence in situ hybridization on both adherent and non-adherent cells. The invention also provides multiplexed detection of nucleic acids, proteins, and cellular activity. The device and methods can be used to assess cellular interactions and to test the effects of antitumor agents.

24 Claims, 7 Drawing Sheets

(52) U.S. Cl.
CPC . *B01L 2200/0668* (2013.01); *B01L 2300/069* (2013.01); *B01L 2300/087* (2013.01); *B01L 2300/0816* (2013.01); *B01L 2300/0819* (2013.01); *B01L 2300/0867* (2013.01); *B01L 2300/0883* (2013.01); *B01L 2400/0487* (2013.01)

(58) Field of Classification Search
CPC ....... B01L 2300/069; B01L 2300/0819; B01L 2300/087; B01L 2300/0883; B01L 2300/0816; B01L 2300/0867; B01L 2200/0668
See application file for complete search history.

(56) References Cited

U.S. PATENT DOCUMENTS

| | | | |
|---|---|---|---|
| 2013/0260447 A1 | 10/2013 | Link | |
| 2015/0346201 A1* | 12/2015 | Korny | G01N 33/56916 506/9 |
| 2016/0177375 A1* | 6/2016 | Abate | C12Q 1/6886 506/9 |

FOREIGN PATENT DOCUMENTS

| | | | | |
|---|---|---|---|---|
| WO | 2014028378 A2 | 2/2014 | | |
| WO | 2015031190 A1 | 3/2015 | | |
| WO | WO-2015031190 A1 * | 3/2015 | ........... | C12Q 1/6881 |
| WO | 2016011387 A1 | 1/2016 | | |
| WO | 2016059302 A1 | 4/2016 | | |
| WO | 2016100977 A1 | 6/2016 | | |

OTHER PUBLICATIONS

CRL-2408_Product-Sheet NK92MI accessed Jul. 29, 2021 on https://www.atcc.org/products/crl-2408 (Year: 2021).*

Matsushita et al "Cancer Exome Analysis Reveals a T Cell Dependent Mechanism of Cancer Immunoediting",Nature. ; 482(7385): 400-404. doi:10.1038/nature10755. (Year: 2012).*

Lagus, Todd P. et al., "High-throuput co-encapsultaion of self-ordered ceil trains: cell pair interactions in microdroplets", RSC Advances, vol. 3, No. 43, Aug. 21, 2013 (Aug. 21, 2013), XP055426002, DOI: 10.1039/c3ra43624a.

* cited by examiner iii. Merging junction    iv. Docking Array

SINGLE CELL FLUORESCENCE IN SITU HYBRIDIZATION IN MICROFLUIDIC DROPLETS

CROSS REFERENCE TO RELATED APPLICATIONS

This application claims the priority of U.S. Provisional Application No. 62/361,035 filed Jul. 12, 2016 and entitled "FISH-DROPS: FLUORESCENCE IN SITU HYBRIDIZATION IN MICROFLUIDIC DROPLETS", the whole of which is hereby incorporated by reference.

STATEMENT REGARDING FEDERALLY SPONSORED RESEARCH OR DEVELOPMENT

This invention was made with government support under grant CA174401 awarded by the National Institutes of Health. The government has certain rights in the invention.

BACKGROUND

The goal of personalized medicine is to deliver highly specialized healthcare to every patient based on their unique biological characteristics. To this end, it is necessary to devise single cell analysis technologies that allow investigation of multiple aspect of cellular responses. Technical advances in single cell analysis have allowed researchers to explore key questions in cellular heterogeneity in areas such as immune response, intratumoral variability, and embryonic development and cell fate decisions. Methods such as quantitative multiplexed RT-PCR and high-throughput transcriptome sequencing (RNA-Seq) have been used to identify heterogeneity in cells of same origin, or identically treated cell population.

However, such approaches to single cell analysis rely on genetic material extracted from cells, which do not permit retention of intracellular spatial resolution of the transcripts. The spatial context of mRNA in cells is important, for instance, as a means of regulating translation locally and fine-tuning protein activity at the local level. Localization of mRNA is known to impact cell development and organ formation. Fluorescence in situ hybridization (FISH) not only preserves the spatial organization of intracellular RNA in individual cells but also quantifies RNA abundance with high resolution. In particular, single molecule-FISH (sm-FISH) has been used to highlight the significance of subcellular RNA localization in cell migration, development, and polarization. However, conventional FISH assays require highly trained personnel, take 2-3 days to complete, and are expensive (approximately $90 per slide), mainly because of the high cost of the probes.

Moreover, characterization of the heterogeneity in immune reactions requires assessing dynamic single cell responses as well as interactions between the various subsets of immune cells. However, there are currently few methods available that allow dynamic investigation of immune cell interactions, and other types of interactions among freely dispersed cells, without physically constraining non-adherent cells.

There is ongoing need for affordable, automated technologies for detection of gene expression at single-cell level, including in non-adherent cells, that will enable personalized medicine at point-of-care and in the field.

SUMMARY OF THE INVENTION

The present invention allows on-chip single-molecule fluorescence in situ hybridization to be performed in single cells, including non-adherent cells. The methods include the use of a dual-array or multiple-array device capable of generating aqueous microdroplets containing cells within a biocompatible matrix. Moreover, the method further enables simultaneous (i.e., multiplexed) detection of nucleic acid species, protein species and cell function using a microfluidic dual-array or multiple-array analysis system. Therefore, the invention allows assessment of cell activity and the correlation of cell activity with nucleic acid expression and/or protein expression.

One aspect of the invention is a method for detecting nucleic acid expression in a single cell, the method including the steps of: (a) providing a fluorescence imaging microscope and a microfluidic device capable of forming an array of aqueous microdroplets in oil, the device comprising first and second translucent microdroplet array chambers; (b) preparing a plurality of first aqueous microdroplets in an oil phase using the microfluidic device, each microdroplet comprising one or more cells, and transporting the plurality of aqueous microdroplets into the first microdroplet array chamber; (c) analyzing the one or more cells of each first microdroplet in the array chamber using the fluorescence imaging microscope for a period of time; (d) transporting the first microdroplets out of the array chamber and through a microdroplet merging device, where the first microdroplets are individually merged with second microdroplets containing a biocompatible matrix precursor to form a plurality of third microdroplets; (e) transporting the third microdroplets into the second microdroplet array chamber and causing the matrix precursor to form a biocompatible matrix embedding one or more cells within each third microdroplet; (f) fixing and permeabilizing the cells embedded within the plurality of third microdroplets; (g) incubating the third microdroplets with one or more fluorescently-labeled oligonucleotide probes; (h) detecting the oligonucleotide probes in individual cells within the third microdroplets in the second microdroplet array chamber using the fluorescence imaging microscope; and (i) determining the expression of one or more nucleic acids in individual cells based on the detected oligonucleotide probes.

The nucleic acid can be any type of nucleic acid, such as DNA, RNA, or artificial (synthetic) nucleic acids or nucleic acid derivatives, also including any chemical modification thereof, and can be either single-stranded, double-stranded, or a mixture of single- and double-stranded. In some embodiments, the nucleic acid is RNA, such as mRNA. The biocompatible matrix can include or consist of any suitable natural or artificial material, such as agarose, alginate, and hydrophilic biocompatible polymers.

The cells can be any type of cells, such as prokaryotic or eukaryotic cells. In some embodiments, the cells are human cells. In some embodiments, the cells are non-adherent cells, such as leukocytes. In some embodiments, the cells are natural killer (NK) cells, T lymphocyte cells, dendritic cells (DC), or a combination thereof. In some embodiments, the cells are tumor cells. In some embodiments, the method includes two or more types of cell, such as an immune cell and a tumor cell.

In some embodiments of the method, after the aqueous microdroplets are formed, additional reagents (e.g., an anti-tumor agent) are added using a droplet merging junction. In some embodiments, after the aqueous microdroplets are formed the microdroplets are sorted and routed to a selected fluidic pathway, chamber, or off-device location, according to an optical signal detected in the aqueous microdroplets.

In some embodiments, the method includes simultaneous analysis of at least 1000 aqueous microdroplets, or at least 2000, at least 3000, at least 4000, at least 5000, at least 10000, at least 15000, or at least 20000 aqueous microdroplets.

In some embodiments, the steps (a) to (h) of the method are performed and completed in 10 hours or less. In some embodiments, step (f) further includes a dehydration step.

In some embodiments, the method further includes detection of one or more protein species in cells within the microdroplets by staining using a probe such as an antibody or aptamer, preferably fluorescently labeled. In some embodiments, the method further includes analyzing cells of the first or third microdroplets for cytotoxicity, i.e., for toxic effects on the cells that can be visualized optically or using a biomarker.

In some embodiments, quantitative analysis of gene expression in two or more cells is obtained following interaction of the two or more cells within a microdroplet. In some embodiments, the method includes simultaneous analysis of at least 1000 groups of two or more interacting cells, or at least 2000 groups, at least 4000 groups, at least 5000 groups, at least 10000 groups, at least 15000 groups, or at least 20000 groups of two or more interacting cells. In some embodiments, one of the two or more interacting cells is an immune cell and another of the two or more interacting cells is a tumor cell. In some embodiments, the immune cell is an NK cell. In some embodiments, the immune cells and tumor cells are present in a ratio from 1:1 to 1:10.

Another aspect of the invention is a microfluidic device for detecting nucleic acid expression in a single cell, the device including: a first inlet for an oil and a second inlet for a first aqueous suspension of cells, wherein the first inlet is fluidically connected to a first microchannel and the second inlet fluidically connected to a second microchannel; a nozzle formed by a T-shaped intersection of the first and second microchannels, the nozzle capable of producing aqueous microdroplets suspended in the oil, the aqueous microdroplets comprising the cells; a first microdroplet array chamber having a first end fluidically connected to the nozzle, a second end fluidically connected to a first end of a droplet merging junction, and a translucent window configured to allow imaging of an array of microdroplets in the first microdroplet array chamber; a second microdroplet array chamber, fluidically connected to a second end of the droplet merging junction; and a third inlet for an aqueous reagent solution, the third inlet connected to the droplet merging junction and configured to provide one or more reagents in aqueous microdroplets for merging with microdroplets transiting through the droplet merging junction from the first microdroplet array chamber to the second microdroplet array chamber.

Yet another aspect of the invention is a system for detecting nucleic acid expression in a single cell, the system including: the microfluidic device described above; a fluorescence imaging microscope; and optionally, an imaging device for forming images of cells in microdroplets in the microfluidic device using the fluorescence imaging microscope; and further optionally, a computer for recording and/or analyzing the images of cells. The invention can be summarized further by the following listing of embodiments.

1. A method for detecting nucleic acid expression in a single cell, the method comprising the steps of:
(a) providing a fluorescence imaging microscope and a microfluidic device capable of forming an array of aqueous microdroplets in oil, the device comprising first and second translucent microdroplet array chambers;

(b) preparing a plurality of first aqueous microdroplets in an oil phase using the microfluidic device, each microdroplet comprising one or more cells, and transporting the plurality of aqueous microdroplets into the first microdroplet array chamber;

(c) observing and/or analyzing the one or more cells of each first microdroplet in the array chamber using the fluorescence imaging microscope for a period of time;

(d) transporting the first microdroplets out of the array chamber and through a microdroplet merging device, where the first microdroplets are individually merged with second microdroplets, or with an aqueous fluid stream, containing a biocompatible matrix precursor to form a plurality of third microdroplets;

(e) transporting the third microdroplets into the second microdroplet array chamber and causing the matrix precursor to form a biocompatible matrix embedding one or more cells within each third microdroplet;

(f) fixing and permeabilizing the cells embedded within the plurality of third microdroplets;

(g) incubating the third microdroplets with one or more fluorescently-labeled oligonucleotide probes;

(h) detecting the oligonucleotide probes in individual cells within the third microdroplets in the second microdroplet array chamber using the fluorescence imaging microscope; and (i) determining the expression of one or more nucleic acids in individual cells based on the detected oligonucleotide probes.

2. The method of embodiment 1, wherein the nucleic acid is mRNA.

3. The method of embodiment 1 or 2, wherein the biocompatible matrix is selected from the group consisting of agarose, alginate, and hydrophilic polymers.

4. The method of any of the preceding embodiments, wherein the cells are non-adherent cells.

5. The method of any of the preceding embodiments, wherein the method comprises observing and/or analyzing two or more types of cells in at least one of the microdroplets.

6. The method of embodiment 5, wherein at least one type of cell is an immune cell and at least one type of cell is a tumor cell.

7. The method of any of the preceding embodiments, wherein one or more additional reagents are added to the first microdroplets after their formation using a droplet merging junction.

8. The method of embodiment 7, wherein at least one of the additional reagents is an antitumor agent.

9. The method of any of the preceding embodiments, wherein the method comprises simultaneous analysis of at least 1000 aqueous microdroplets.

10. The method of embodiment 9, wherein the method comprises simultaneous analysis of at least 4000 aqueous microdroplets.

11. The method of any of the preceding embodiments, wherein aqueous microdroplets are sorted and routed to a selected fluidic pathway, chamber, or off-device location, according to an optical signal detected in the aqueous microdroplets.

12. The method of any of the preceding embodiments, wherein steps (a) to (h) are performed in 10 hours or less.

13. The method of any of the preceding embodiments, wherein step (f) further comprises a dehydration step.

14. The method of any of the preceding embodiments, further comprising detection of a protein species by antibody staining.

15. The method of any of the preceding embodiments, wherein the method further comprises analyzing cells of the first or third microdroplets for cytotoxicity.

16. The method of any of the preceding embodiments, wherein quantitative analysis of gene expression in two or more cells is obtained following interaction of the two or more cells within a microdroplet.

17. The method of embodiment 16, wherein the method comprises simultaneous analysis of at least 1000 groups of two or more interacting cells.

18. The method of embodiment 17, wherein the method comprises simultaneous analysis of at least 4000 groups of two or more interacting cells.

19. The method of any of embodiments 16-18, wherein one of the two or more interacting cells is an immune cell and another of the two or more interacting cells is a tumor cell.

20. The method of embodiment 19, wherein the immune cell is an NK cell.

21. The method of embodiment 19 or 20, wherein immune cells and tumor cells are present in a ratio from 1:1 to 1:10.

22. A microfluidic device for detecting nucleic acid expression in a single cell, the device comprising:
a first inlet for an oil and a second inlet for a first aqueous suspension of cells, wherein the first inlet is fluidically connected to a first microchannel and the second inlet fluidically connected to a second microchannel;
a nozzle formed by a T-shaped intersection of the first and second microchannels, the nozzle capable of producing aqueous microdroplets suspended in the oil, the aqueous microdroplets comprising the cells;
a first microdroplet array chamber having a first end fluidically connected to the nozzle, a second end fluidically connected to a first end of a droplet merging junction, and a translucent window configured to allow imaging of an array of microdroplets in the first microdroplet array chamber;
a second microdroplet array chamber, fluidically connected to a second end of the droplet merging junction; and
a third inlet for an aqueous reagent solution, the third inlet connected to the droplet merging junction and configured to provide one or more reagents in aqueous microdroplets for merging with microdroplets transiting through the droplet merging junction from the first microdroplet array chamber to the second microdroplet array chamber.

23. A system for detecting nucleic acid expression in a single cell, the system comprising:
the microfluidic device of embodiment 22;
a fluorescence imaging microscope; and
optionally, an imaging device for forming images of cells in microdroplets in the microfluidic device using the fluorescence imaging microscope; and
optionally, a computer for recording and/or analyzing the images of cells.

DETAILED DESCRIPTION OF THE INVENTION

Figure 1:
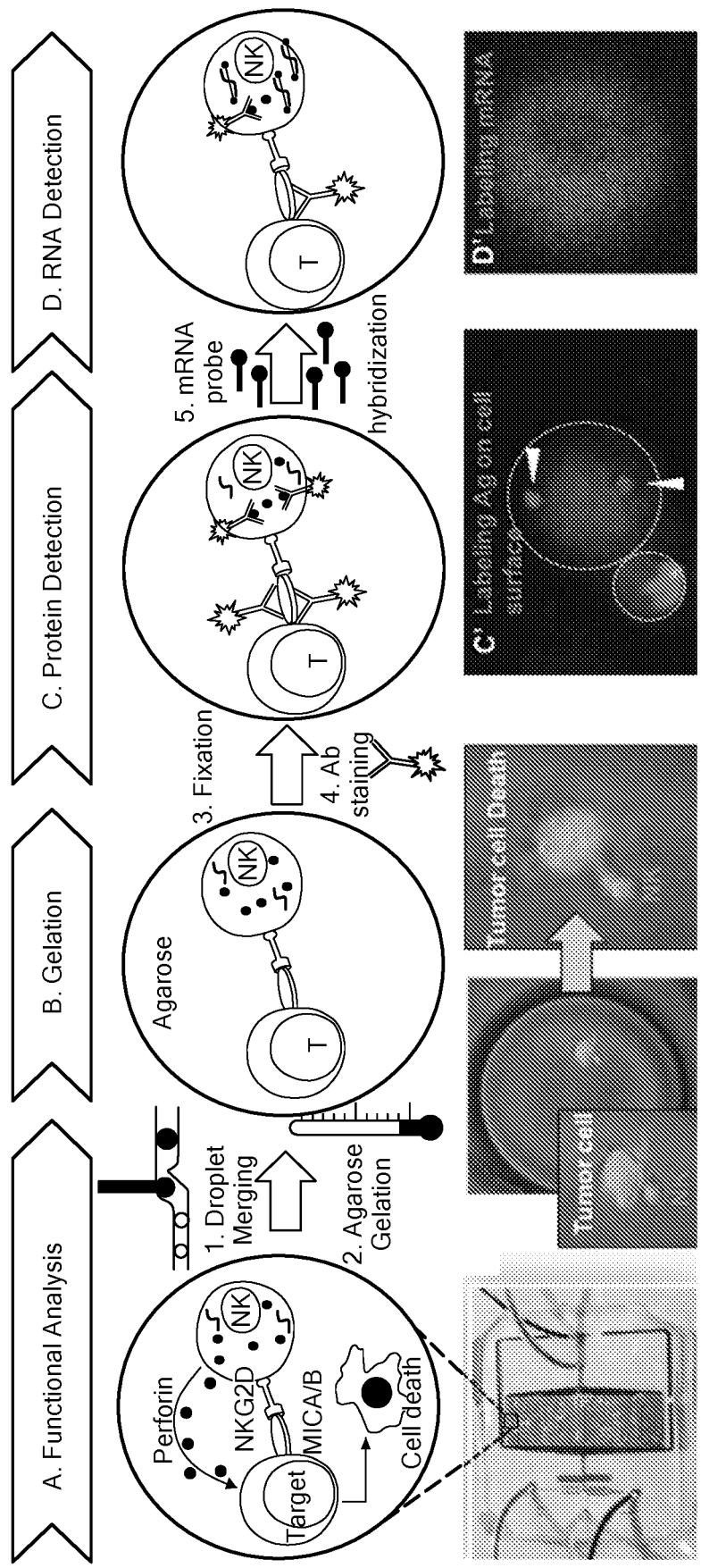
FIG. 1 shows a schematic representation and microscopic images of the microfluidic droplet system.

The present invention provides methods and devices for fast and automated detection of nucleic acid expression at the single-cell level, suitable for the simultaneous characterization of large numbers of individual cells and interacting cells. The method enables high throughput characterization of synaptic communication, cellular activity, cytotoxicity and genetic fluctuation in the same system (FIG. 1). The invention is useful to characterize, analyze, or screen single cell behavior, where it is important to visualize nucleic acid expression, cellular activity and/or endogenous protein concurrently in the same cell, such as antigen-specific lymphocyte activation, pathogen-stimulated macrophage response, effect of therapeutics on cancer cells, and preclinical assessment of cellular immunotherapies.

The method employs a microfluidic device for the formation and analysis of aqueous microdroplets containing one or more types of cells. Cells suspended in an oil medium are encapsulated in picoliter-volume aqueous microdroplets and directed, sorted, and arranged by the microfluidic device into one or more arrays for analysis. Various reagents for the analysis can be added to the droplets at formation or by later merger of droplets (i.e., by merger of droplets together or merger of droplets with a stream of aqueous solution entering an oil phase). Such reagents include polymers, biocompatible matrices, antibody-conjugated microspheres, fluorescent detection antibodies, cell viability indicators, therapeutic drugs, and other cells for cell-cell interaction studies. The analysis of single droplets provides high sensitivity and short reaction times.

Figure 2A:
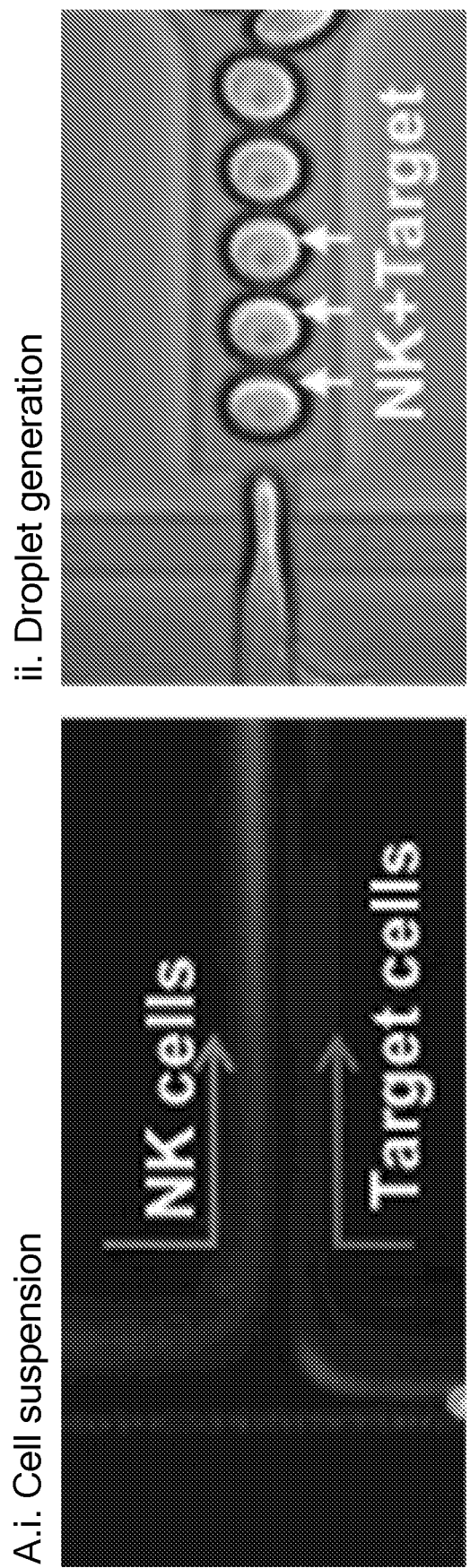
FIGS. 2A-D show a schematic representation and microscopic images of cell encapsulation in the microfluidic droplet system.

The strategy of forming cell-containing microdroplets is described in PCT publication WO 2015200832, which is hereby incorporated by reference. Briefly, a series of aqueous droplets are formed in an oil (such as mineral oil, silicone oil, or a vegetable oil, the oil optionally including a low concentration of a surfactant to improve flow characteristics) using a nozzle containing a T-shaped junction in a microfluidic device (i.e., a device for handling fluids that has at least one channel of diameter in the range from 1 to 999 microns). The droplets are substantially spherical, and their aqueous contents include a suspension of one or more types of individual cells. The droplets as formed can also include one or more cells or mixtures of different types of cells. The cells can be any type of cell including, for example, tumor cells (including tumor stem cells and model tumor cells), cells of a cell line or culture, cells from a patient, immune cells such as lymphocytes or macrophages, stromal cells, or fibroblasts. Solutions can be added to the microfluidic device from syringes, which can be operated by independent syringe pumps. In some embodiments, additional reagents, such as microsphere sensors, antibodies, and drugs are added through one of the cell suspension inlets. In some embodiments, two or more aqueous suspensions containing cells (FIG. 2A.i) are flowed into the T-shaped junction of the device and form cell-containing microdroplets (FIG. 2A.ii).

The strategy and device for obtaining multiplexed detection of cell function, protein expression and nucleic acid expression are described herein. The claimed device employs a dual-array design to allow identification of individual droplets from their respective position in the arrays, to track the same cells over time and to correlate function and protein/nucleic acid expression in individual droplets. The device includes two translucent or transparent microdroplet array chambers connected via a droplet merging junction. "Array chamber", "docking array" and "trapping array" are used interchangeably herein.

Once generated, the droplets can be deposited into a first docking array where the cells can be monitored for a variety of parameters (e.g., viability, growth, proliferation, development, motility, intercellular interaction, and interactions with the polymer scaffold or with extracellular matrix components) for the desired period of time. Cells encapsulated in the droplets have been shown to survive for long periods due to the gas exchange capability of the materials used to construct the device, such as poly-dimethylsiloxane (PDMS). In some embodiments, cells are monitored for 24 h to 48 h in the first array.

Figure 2B:
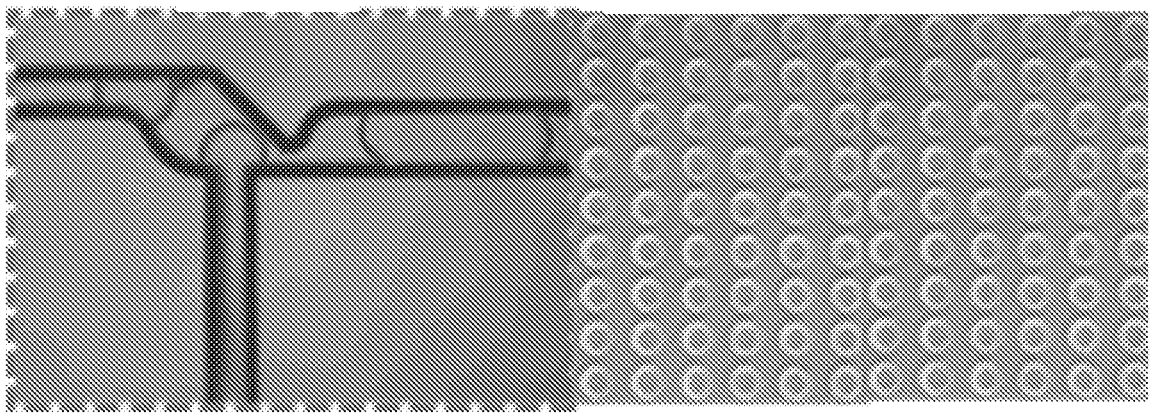
Figure 2B:
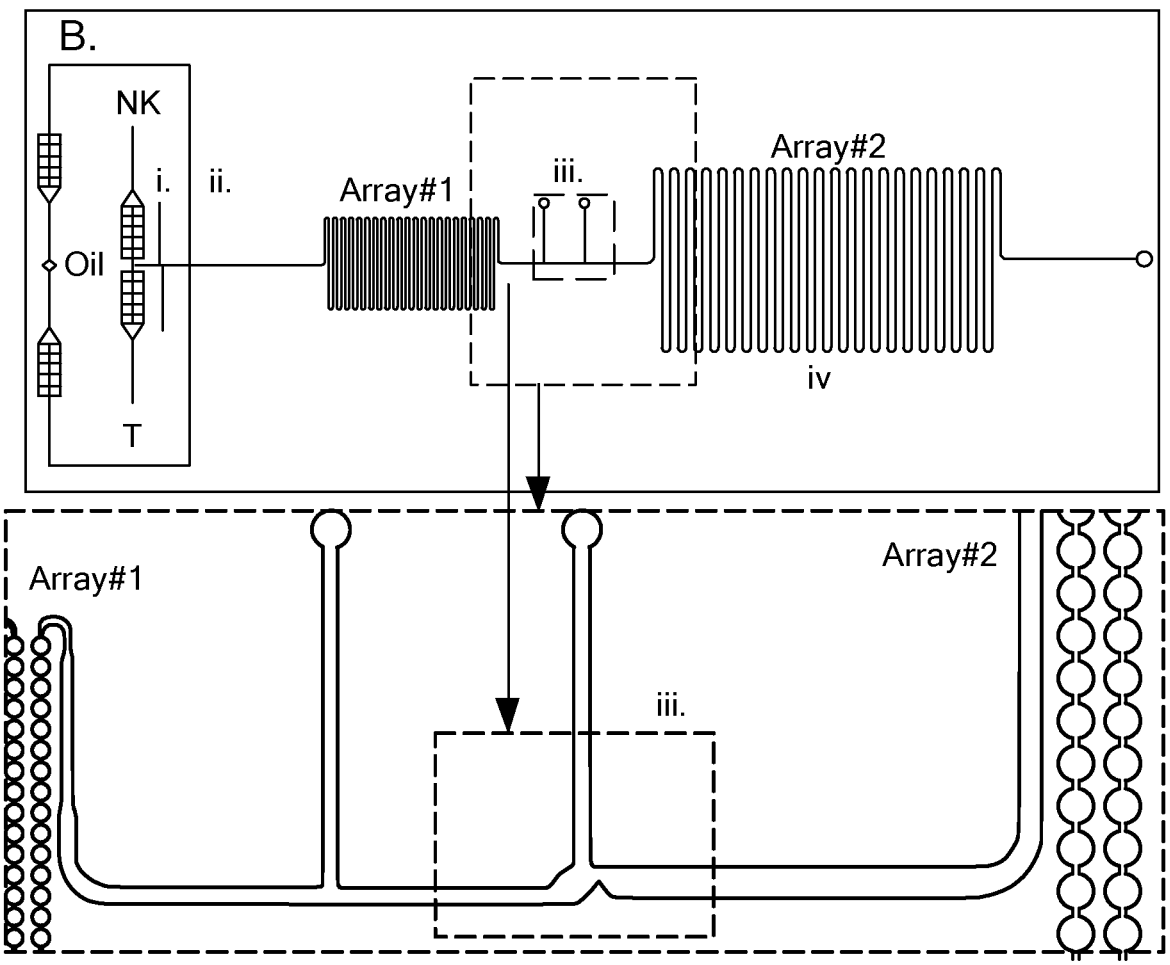

Following encapsulation of cells and docking in the first trapping array, the liquid-phase microdroplets can be converted into solid or gel phase, preferably by the formation within the droplet of a polymer network that entraps the cells into discrete structural units mirroring the original droplets, while still allowing solution exchange or the diffusion of reagents, such as oligonucleotide probes, antibodies, or aptamers, to the cells. To this end, cell-containing droplets can be merged with droplets including or consisting of a biocompatible matrix or a biocompatible matrix precursor. One example of a droplet merging method is described by Hondroulis et al (Biotechnology and Bioengineering, Vol. 114, No. 3, March 2017, pp 705-709) which is hereby incorporated by reference. In that method, cell-containing droplets are driven toward a merging junction by fluid pressure, where a "pinched neck" constriction decreases droplet velocity significantly (see, e.g., FIG. 2B.iii). At the merging area, the droplets are contacted with a second flow stream, introduced into the device through a specifically designated inlet. The T-shaped droplet-merging junction contains an expansion region upstream and a constricted neck downstream of the T-region. This forces prolonged contact with a biocompatible matrix precursor stream, leading to droplet merging. The merged droplet increases in volume until it contacts the angled wall of the constriction. Once contact is made, continuous phase flow is blocked, and the droplet is forced through the constriction and breaks off. This provides merged droplets of consistent volume resulting in a composite cell/biocompatible matrix droplet. The merging of the droplets is apparent by the change in diameter of the droplets. Droplet merging happens at a fast time-scale, from microseconds to a few milliseconds, thereby minimizing or avoiding disturbing the live cells contained in the droplets. The merged droplets, now containing cells and a liquid or non-polymerized form of the biocompatible matrix (or biocompatible matrix precursor) are then trapped in a second docking array (FIG. 2B.iv). The outflow of the droplets from the first docking array (Array #1, FIG. 3) enter the second docking array (Array #2) sequentially, arresting in a "first-come-last-seated" order. That is, the first droplet to enter Array #2 will be captured in the farthest trapping site of Array #2, and so on. In some embodiments, the first (or upper) array is located in a superior position in relation to the second (or lower) array. The device can have any number of trapping arrays, such as 1, 2, 3, 4, 5, 6, 7, 8, 9, 10, or more arrays. In some embodiments, each of the arrays includes at least 1000 trapping sites, such as at least 2000, at least 3000, at least 4000, at least 5000, at least 6000, at least 7000, at least 8000 or at least 9000 trapping sites. In some embodiments, each of the arrays includes at least 10000 trapping sites, such as at least 12000, at least 15000, or at least 20000 trapping sites. Hence, the dual-array design of the present microfluidic device entails sequential connections between the consecutive rows, ensuring that release and capture of the droplets occur consecutively. The close proximity of the encapsulated cells, as well as the accumulation of secreted cell factors (such as cytokines and exosomes), ensures that cells encapsulated in every droplet have a very high probability of interaction and subsequent activation, minimizing variability at the local level and providing more control over direct cell pairing.

Solid-phase microdroplets are obtained by polymerization, solidification, sol-gel transition or by any other mechanism that increase the viscosity of the biocompatible matrix or biocompatible matrix precursor in the aqueous microdroplets. In some embodiments, the biocompatible matrix is agarose, and gelation is achieved by lowering the temperature of the filled droplet array to promote the sol-gel transition of the ultra-low temperature gelling agarose. This results in embedding of the encapsulated cells in discrete agarose matrices in the docking array. Agarose is a linear polysaccharide consisting of alternating residues of β-1,3-linked-D-galactose and a-1,4-linked 3,6-anhydro-L-galactose. Aqueous agarose solutions form gels upon cooling, due to the aggregation of double helices formed by the physical entanglement of anhydro bridges on the individual molecules. Solutions of low-gelling temperature agarose are particularly useful for cell encapsulation. At moderately high concentrations, they are liquid at a temperature of 37° C., and below 20° C. they gel, and upon heating to 37° C. they remain gel-like. The concentration of agarose used for cell encapsulation can be 0.5%-5% w/v, preferably 0.5%-2.5 w/v %, and can be prepared in complete cell growth medium.

In some embodiments, polymerization is achieved by contacting the polymer or polymer precursor with a polymerization-inducing agent. In some embodiments, the polymerization-inducing agent is a chemical agent, such as a cationic compound, an anionic compound, free radicals, a free radical precursor, and combinations thereof. In some embodiments, polymerization is induced by a physical agent, such as ionizing and/or non-ionizing radiation.

In some embodiments, the polymer is sodium alginate, and polymerization of sodium alginate is achieved by contacting alginate with a polymerization mediator or catalyst, such as $CaCl_2$. The $Ca^{2+}$ ions (or any other suitable divalent or trivalent cation that promotes alginate polymerization) cause the formation of a network of polymerized alginate fibers within the droplets within minutes after mixing at the nozzle, resulting in formation of a polymer scaffold for cell attachment. Many other suitable polymers and corresponding polymerization mediators can be used. For example, the polymer can be formed from collagen (polymerized by a pH elevation), polyethylene glycol (PEG, polymerized using UV light directed at an appropriate zone of the microfluidic device), or chitosan.

The cells preferably adhere to the biocompatible matrix scaffold and grow, differentiate, and/or proliferate within the droplet. The present method has the advantage of enabling evaluation even of non-adherent cells, such as hematopoietic cells. By isolating single cells in microfluidic chambers before cell analysis it is possible to prevent homotypic signaling mediated by secreted factors prior to nucleic acid analysis. The present method decreases communication between neighboring cell pairs, preserving the integrity of single-cell analysis approach.

A device containing the microdroplets can be placed in to a typical cell culture incubator for a period of hours, days or weeks and removed periodically for monitoring. The device can be configured to fit onto a standard stage of an inverted light microscope, such as a fluorescence microscope, and the device also can optionally include a transparent or translucent window covering the incubation chamber containing the microdroplets, so as to permit non-disruptive microscopic observation of the spheroids. The device also can optionally include a separate perfusion pathway to allow perfusion of the spheroids individually, collectively, or in groups with desired media containing a variety of agents. Such agents can include, for example, known or candidate antitumor agents, peptides, cytokines, antibodies, aptamers, nucleic acids, nucleotides, siRNA, antisense RNA, cell adhesion molecules or inhibitors of cell adhesion such as RGD peptides, receptor agonists or antagonists, labeled compounds such as fluorescent compounds or antibodies.

Following gelation, polymerization or solidification, the stable microdroplets can be washed by flowing a washing solution through the device to remove the oil phase. In some embodiments, the washing solution includes water. In some embodiments, the washing solution includes a buffer, such as 1xPBS buffer. In some embodiments, the washing solution includes an organic solvent, such as acetone or isopropyl alcohol.

Following washing of the oil phase, cells can be optionally fixed, dehydrated and permeabilized according to any methods known in the art. In some embodiments, the cells are not fixed before hybridization with labeled probes Examples of suitable fixatives include aldehydes (e.g., paraformaldehyde, formaldehyde and glutaraldehyde), alcohols (e.g., ethanol and methanol), other organic compounds (e.g., acetone and acetic acid), and combinations thereof. In some embodiments, the fixative is a 1-4% solution of formaldehyde, alcohol and/or methanol. Dehydration can be performed as a single step or a series of sequential steps. In some embodiments, dehydration is conducted by sequentially incubating the microdroplet array with solutions containing 70%, 90% and 100% ethanol. Examples of suitable permeabilizers include enzymes (e.g., proteinase K and streptolysin), detergents (saponin, sodium dodecyl sulfate, Triton, Tween 20, and NP40), and combinations thereof. In some embodiments, the permeabilizing agent is Triton-X-100. In some embodiments, the permeabilizing agent is a lysis buffer containing 1% SDS and proteinase K.

Following fixation and permeabilization, cells can be contacted with labeled antibodies (for protein detection) and/or with a hybridization buffer (for nucleic acid detection). Labeled antibodies can be used to identify the presence and quantity of specific proteins or antigens, as well as their spatial distribution within a cell. Any immunocytochemistry method know in the art can be used with the present device and methods to enable high-throughput protein detection and quantification, even in non-adherent cells.

The hybridization buffer contains labeled probes, such as fluorescently-labeled DNA or RNA probes. In some embodiments, the fluorescently-labeled probes are VIEWRNA Cell Plus Assays probes (Affymetrix eBioscience) that can generate enhanced signals due to branched DNA amplifications. The probes can have any suitable length. In some embodiments, the probes are from about 15 to about 50 nucleotides in length. In some embodiments, the probes include about 20 base pairs. The duration and temperature of incubation can be optimized taking into consideration probe characteristics and pore sizes in the biocompatible matrix, among other variables. In some embodiments, the temperature of hybridization is from about 37° C. to about 65° C.

Quantitative information about nucleic acid expression and/or protein expression can be obtained by performing microscopic imaging of the microdroplet array, such as time-lapse fluorescence microscopy. The microfluidic device containing cell-encapsulated droplets can be maintained in a humidified microscopic stage-top incubator at 37° C. and 5% $CO_2$ for the duration of the experiment, up to 48 hours, for example. Time-lapse images can be obtained by any suitable automated software control. The array can be scanned to identify locations containing the desired cell numbers. In some embodiments, the specific x-, y-, and z-positions are programmed in an imaging program associated with the microscope workstation being utilized (e.g., Zen imaging software for Zeiss microscopes). Images of these locations can be obtained at desired interval (such as every 5 minutes, every 15 min, every 30 min, or longer). Image processing and analysis can be done with ImageJ (rsb.info.nih.gov/ij/), Microsoft Office Excel, and commercially available statistical software (e.g., GraphPad or Origin Pro). Fluorescent intensity of the cells at any time point can be analyzed by selecting a region of interest (i.e., the cell body) and measuring mean intensity in the image processing software. In some embodiments, normalized fluorescent intensity (NFI) for each cell is calculated as a ratio of fluorescent intensity at every time point with respect to fluorescent intensity at the initial time. Contact periods can be defined as cells forming visible conjugates for at least two consecutive time points. In some embodiments, all periods of association and dissociation are counted for each cell and represented as percentage of total cells can be analyzed.

The method of the invention presents a number of advantages over previous methods. It allows analysis of non-adherent cells (such as immune cells) without the need for immobilization. To date, on-chip FISH techniques have allowed only analysis of adherent cells, or of non-adherent cells that have been previously immobilized. However, immobilizing cells on antibody or receptor ligand-conjugated surfaces can lead to unintended activation of intracellular signaling. In addition, previous on-chip FISH assays do not isolate single cells in microfluidic chambers before cell analysis. Therefore, these cells are likely to undergo homotypic signaling mediated by secreted factors prior to FISH analysis.

Another advantage of the invention is the rapid mixing and reaction kinetics of the microfluidic droplet system, which reduce assay duration significantly ≤10 hrs while minimizing sample and reagent volume and reducing overall cost of the procedure 10 to 20 fold. In conventional FISH assays, hybridization takes a prolonged period of time (usually overnight) because the reaction relies on diffusion-limited hybridization. In some embodiments, the present method reduces by at least 40% the quantity of labeled probes necessary for completing an immunocytochemical assay or a FISH assay. In some embodiments, the present method reduces by at least 50% the time necessary for the completion of an immunocytochemical assay or a FISH assay.

The size of a cell-containing microdroplet can vary in the range from about 50 microns to about 900 microns in diameter, and is substantially determined by: the size of the polymer scaffold to which the cells are bound; device design (such as the size of the trapping sites in an array); and the flow rates of the oil and aqueous phases. Exemplary flow rates are as follows. For the flow of oil into the oil inlet: 650-1100 µl/hr, 650-1000 µl/hr, or 800-1000 µl/hr. For the flow of cell suspension into the cell inlet: 200-300 µl/hr, 250-300 µl/hr, or 300-400 µl/hr. Suitable flow rates can be readily ascertained and optimized by routine experimentation with a given device.

By coordinating individual inlet flow rates and optimizing initial cell density (such as in the range of about 1 million/mL to about 2 million/mL), large numbers of droplets can be routinely obtained which co-encapsulate the desired number of types of individual cells. Each microdroplet can include one or more cells. For example, the average number of cells in each droplet can be one or more, such as 1, 2, 3, 4, 5, 6, 7, 8, 9, 10, or more. The number of cells encapsulated in the microdroplets is a Poisson probability-regulated process. It is expected that within any population of microdroplets a number of microdroplets will have more or fewer cells than the average for that population.

In some embodiments, a single cell type is encapsulated in each droplet (though more than a single cell of that type can be encapsulated in each droplet). In some embodiments, the single cell type is a tumor cell, and the present method and device can be used for clinical or preclinical assessment of an antitumor treatment, such as an antitumor drug. In some embodiments, after droplet formation and consequent cell encapsulation, a solution containing a known or potential antitumor agent is contacted with the droplet array. The tumor cell can be evaluated in a number of parameters (e.g., viability, growth, proliferation, development, motility, and interactions with the polymer scaffold or with extracellular matrix components) for the desired period of time. In addition, gene and/or protein expression can be assessed, allowing the correlation between phenotypic markers of cell activity and gene up/down-regulation and protein expression. Genes of interest include genes encoding tumor antigens NY-ESO-1, mesothelin, PSA, MART-1, MART-2, Gp100, tyrosinase, p53, ras, MUC1, SAP-1, survivin, CEA, Ep-CAM, Her2, BRCA1/2 and combinations thereof. By assessing gene expression for any desired length of time before, during and after contacting a tumor cell with a treatment, it is possible to investigate how the treatment changes (or fail to change) the transcription and/or translation of any gene. This information can be used to assess the effects of effective and ineffective cancer treatments on gene expression of cancer cells, including specific subsets of cancer cells, such as cancer stem cells or the cells of a particular patient. In addition, by allowing the correlation between gene and protein expression, the present device and methods allow a deeper understanding of the spatial and temporal relations between gene expression and protein production in a cell.

In some embodiments, the cells are derived from a human or non-human subject displaying or suspected of displaying a chromosomal abnormality, such as aneuploidy, or structural alterations such as deletions, duplications, translocations, inversions, insertions, and rings. In some embodiments, the claimed method is employed to detect a disease associated with a chromosome abnormality, such as leukemias, lymphomas, Down Syndrome, Turner Syndrome, Klinefelter Syndrome, Cri-du-Chat Syndrome, and Williams Syndrome. In some embodiments, the method is employed for diagnosis of graft-versus-host disease (GVHD). In some embodiments, the claimed method is employed for the prenatal or preimplantation diagnosis of chromosomal abnormalities in a fetus or embryo. In some embodiments, the claimed method is employed to identify gene expression patterns associated with embryo development and cell fate decisions, as well as the correlation of such patterns with protein expression and cell activity.

In some embodiments, droplets with different compositions can be merged. Each microdroplet can contain a type of cargo, e.g., cells, reagents, drugs, sensors and/or peptides. The claimed method precludes the use of complex electric-coalescence or harsh chemical methods due to the specially designed "pinched neck" geometry. In some embodiments, one or more additional reagents are added to the aqueous microdroplets after their formation using a droplet merging junction. Such agents can include, for example, known or candidate antitumor agents, peptides, cytokines, antibodies, aptamers, nucleic acids, nucleotides, siRNA, antisense RNA, cell adhesion molecules or inhibitors of cell adhesion such as RGD peptides, receptor agonists or antagonists, labeled compounds such as fluorescent compounds or antibodies.

Further disclosed herein is a method for quantitative analysis of gene expression during the interaction of two or more types of cells, optionally combined with analysis of protein expression and/or cell function. Intercellular communication is one of the key features of cell response in vitro or in vivo, but population-level studies can neither provide details about the rapidity or level of activity of each cell (e.g., resting vs. active) nor classify interaction kinetics of individual cells. The present method allows quantification of gene expression, protein expression and/or cell function of hundreds or thousands of cell pairs simultaneously. In some embodiments, the method allows simultaneous analysis of at least 1000 microdroplets, such as at least 4000, at least 5000, at least 6000, at least 7000, at least 8000, at least 9000, or at least 10000 microdroplets.

In some embodiments of the method, a first type of cell and a second type of cell are encapsulated in the same microdroplet. In some embodiments, the first type of cell is an effector cell and the second type of cell is a target cell. In some embodiments, the effector cell is an immune cell and the target cell is a tumor cell. In some embodiments, the effector cell is an immune cell and the target cell is an infectious agent. Examples of immune cells include natural killer (NK) cells, T cells and other leukocytes. The cancer cells can be, for example, derived from a solid tumor, liquid tumor, hematologic tumor, renal cell cancer, melanoma, breast cancer, prostate cancer, testicular cancer, bladder cancer, ovarian cancer, cervical cancer, stomach cancer, esophageal cancer, pancreatic cancer, lung cancer, neuroblastoma, glioblastoma, retinoblastoma, leukemia, myeloma, lymphoma, hepatoma, adenoma, sarcoma, carcinoma, blastoma, or cancer of the colon, lung, kidney, liver, endometrium, cervix, ovary, thyroid, skin, or central nervous system. Infectious agents can be bacterial, viral, and/or parasitic agents such as the etiologic agents of tuberculosis, HIV and malaria. The claimed method can be used to test immunoregulation by cytotoxic lymphocytes cells, activity of cancer-associated immune cells and metabolic inhibitors of NK/T cell activity, among other applications, as well as to analyze changes in gene and/or protein expression associated with these phenomena. The present method further allows analyzing the time-course of these events and the spatio-temporal association between phenotypic markers of cell activity and gene/protein expression.

In some embodiments of the method, T cells are encapsulated with infectious agents or tumor cells. In some embodiments, the T cells are CAR-T cells. T cells, including CAR-T cells, can vary in a number of characteristics, including cytotoxicity and antigen specificity. The present method allows the high-throughput assessment of the interaction between T cells and their targets both in terms of cell activity and in regards to cell gene/protein expression. T cell genes of interest include genes encoding cytokines produced by T cells, such as interleukin (IL)-2, tumor necrosis factor (TNF)-alpha, and interferon gamma; clusters of differentiation (CD) displayed by T cells such as CD45, CD3, CD4, and CD8; and transcription factors involved in immune response such as NF-κB, CREB, Ets-like protein-1, AP-1, and STAT.

Since cell pairs can be encapsulated together within a microdroplet and monitored for the desired period of time, the present method allows high-throughput quantification of single as well as serial interactions between the same cell pair. In addition, it is possible to obtain any effector cell: target cell (E:T) ratio as desired by simply adjusting the initial cell density. This allows characterization of one-to-one interactions as well as one-to-many interactions between the first and the second types of cells, which can be studied in the same experiment. This is an important consideration for certain types of cells, such as NK cells. NK cells are effector immune cells that regulate anti-tumor and anti-pathogenic response. Functionally, NK cells are very heterogeneous: a small subset of NK cells causes a majority of target cell deaths, killing target cells serially, while the remaining NK cells are distinctly less cytotoxic. These cells are also highly dynamic and form fast-acting synapses in a matter of minutes. Currently these aspects are evaluated in vitro using population-level assays, flow cytometry and genetic manipulation, which do not allow continuous dynamic analysis of the same cell. The claimed method allows determination of the extent of so-called "serial killers", i.e., highly cytotoxic NK cells, in a queried population. The close proximity of the encapsulated cells, as well as the accumulation of secreted cytokines and exosomes, ensures that immune cell and target cells in every droplet have a very high probability of interaction and subsequent activation, minimizing variability at the local level and providing more control over direct cell pairing. This technology can be used to screen preclinical samples in order to predict patient-specific responses to NK cell-based therapy. The approach can be further extended to study cytotoxic T lymphocytes and aid in the comprehensive analysis of immunotherapeutic cells such as CAR-T and CAR-NK cells.

In some embodiments of the method, three or more types of cells are encapsulated in the same microdroplet. In some embodiments, a first type of cell is an effector cell, such as a T cell or an NK cell; a second type of cell is an antigen-presenting cell, such as a dendritic cell (DC); and a third type of cell is a tumor cell. In some embodiments, the present method can be employed for high-throughput assessment of cancer vaccines, such as the clinical and preclinical evaluation of DC vaccines.

EXAMPLES

Example 1. Microfluidic Device Fabrication

The microfluidic devices were fabricated by standard soft-lithography protocols. The device design was formulated using CAD (CAD/Art Services, Bandon, Oreg.) and printed on a transparency photomask (Fine Line Imaging, Colorado Springs, Colo.). The design was transferred to clean silicon wafers via UV photolithography utilizing a negative photo resist SU-8 2100 (MicroChem, Newton, Mass.), which was spin-coated on the wafers to obtain a layer of 150 µm height. The wafers served as master templates for elastomeric device fabrication. The prepolymer poly(dimethylsiloxane) (PDMS) (Sylgard 184, Dow Corning, Midland, Mich.) was mixed with the silicone elastomer curing agent at 10:1 ratio (w/w), dispensed over the wafer, degassed and cured for 12 hours at 65° C. The PDMS layer containing the design network was then peeled from the wafer and separated into individual devices. Microscope slides were subjected to plasma oxidation for 30-60 sec and bonded with the PDMS devices by heating at 90° C. for 10 minutes.

Each inlet of the device was connected to individual syringes containing aqueous (i.e., cell suspension in media) or oil-based fluids through Tygon Micro Bore PVC tubing of the following dimension: 0.010" ID, 0.030" OD, 0.010" wall (Small Parts Inc., Fla., USA). The device was treated with Aquapel glass treatment (Aquapel, Pittsburg, USA) for 15 minutes, then flushed with air immediately before experiments. The syringes were operated by individually programmable syringe pumps (Harvard Apparatus, USA). The oil to aqueous flow rates were generally maintained at a ratio of 4:1 to obtain optimal droplet sizes. Experimentally, aqueous flows rates vary from 200-400 µL/hr and oil flow rates vary from 800-1100 µL/hr. The oil phase consisted of Fluorinert® FC-40 (Sigma, St. Louis, Mo.) supplemented with 2% w/w surfactant (008-FluoroSurfactant, Ran Biotechnologies, Beverly, Mass.).

Example 2. Formation of Discrete Microscale Agarose Matrix

Figure 2C:
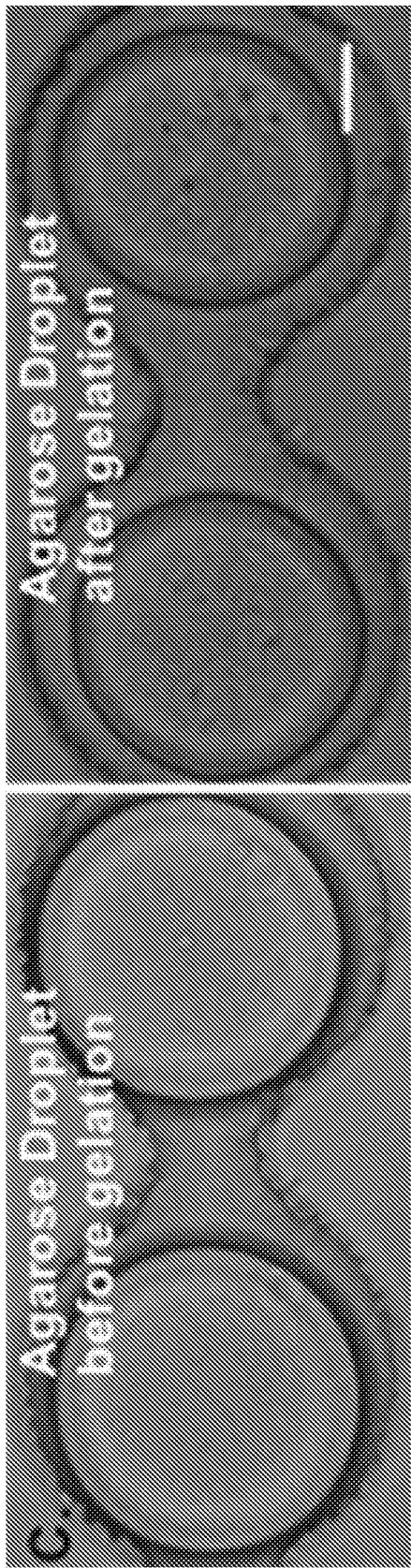

Cultured cells were purchased from commercially available sources (e.g., American Type Culture Collection (ATCC, Manassas, Va.)) and maintained in RPMI-1640 medium supplemented with 10% fetal bovine serum and 1% Antibiotic-Antimycotic solution (Corning Cellgro, Manassas, Va.). All cells were grown at 37° C. under 5% $CO_2$ in a humidified atmosphere. Cells were routinely passaged every three days and harvested at a density of $1\times10^6$ viable cells/mL. A 1.8% ultra-low temperature gelling agarose solution was merged with the formed droplets and subsequently arrested in the docking array. Cooling of the array resulted in gelation of agarose (FIG. 2C). The agarose droplets remained stable in the array for days under perfusion.

Example 3. Fluorescence in Situ Hybridization in Microdroplets

Figure 2D:
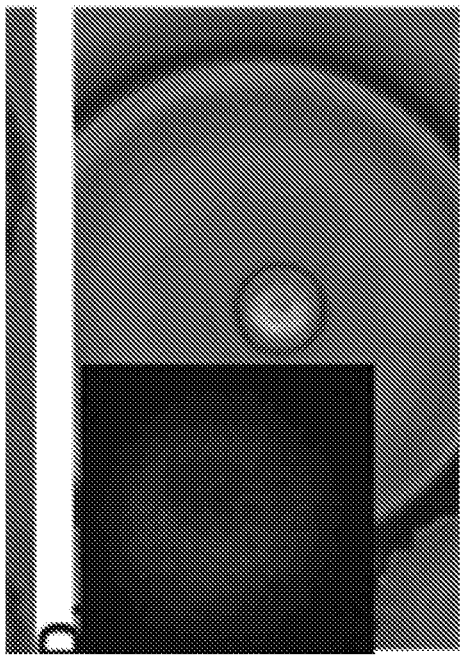

Detection of ABCB1 mRNA in droplet-encapsulated live MCF-7 cells was performed using SmartFlare nanoprobes (EMD Millipore, Billerica, Mass.). Cy5-conjugated ABCB1 mRNA (#SF-2394, Millipore) stock solution was diluted as per the manufacturer's instructions. The final ratio of cells to the diluted probe was maintained at $1\times10^6$ cells: 100 µL. The probes and cells were incubated through separate inlets and maintained in the dark for 24 h. The cells were periodically imaged using a Cy5 filter (FIG. 2D).

Example 4. Monitoring of NK Cell Cytolytic Activity

Figure 4A:
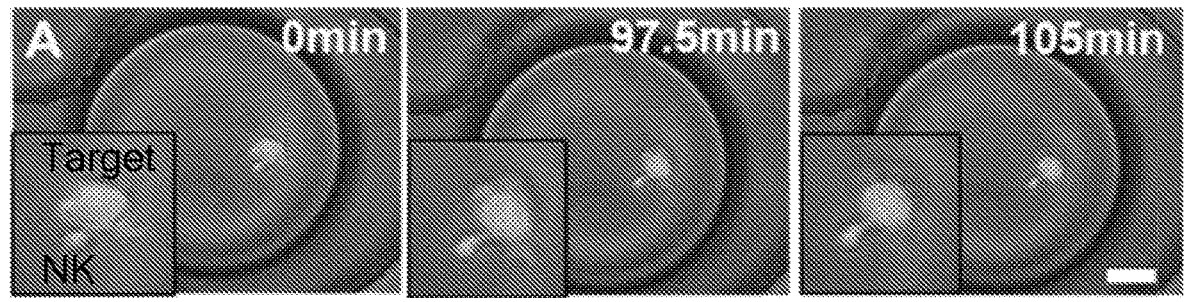
FIGS. 4A-E show the interaction of NK cells and cancer cells within the microfluidic droplet system.
Figure 4B:
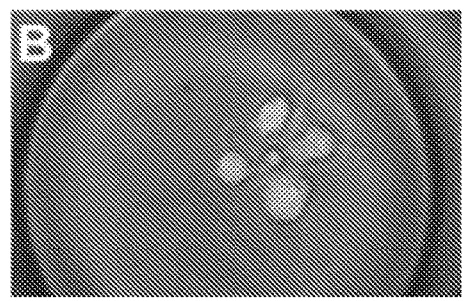
Figure 4C:
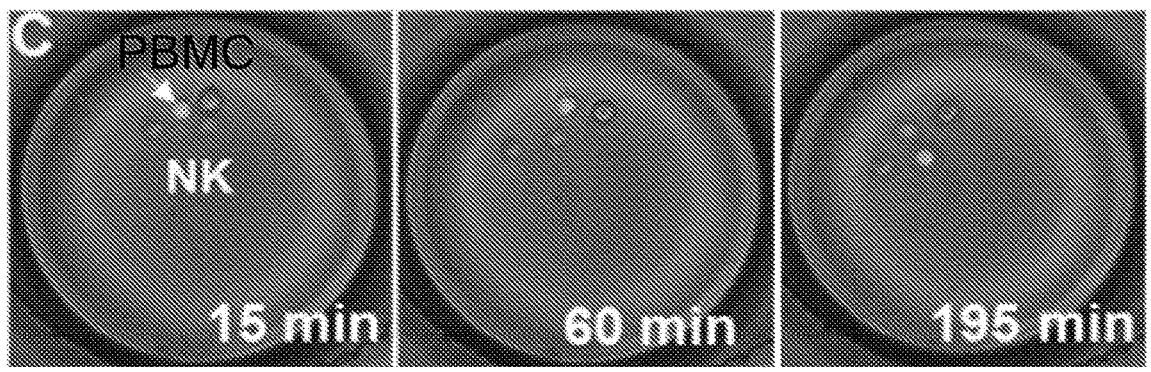
Figure 4D:
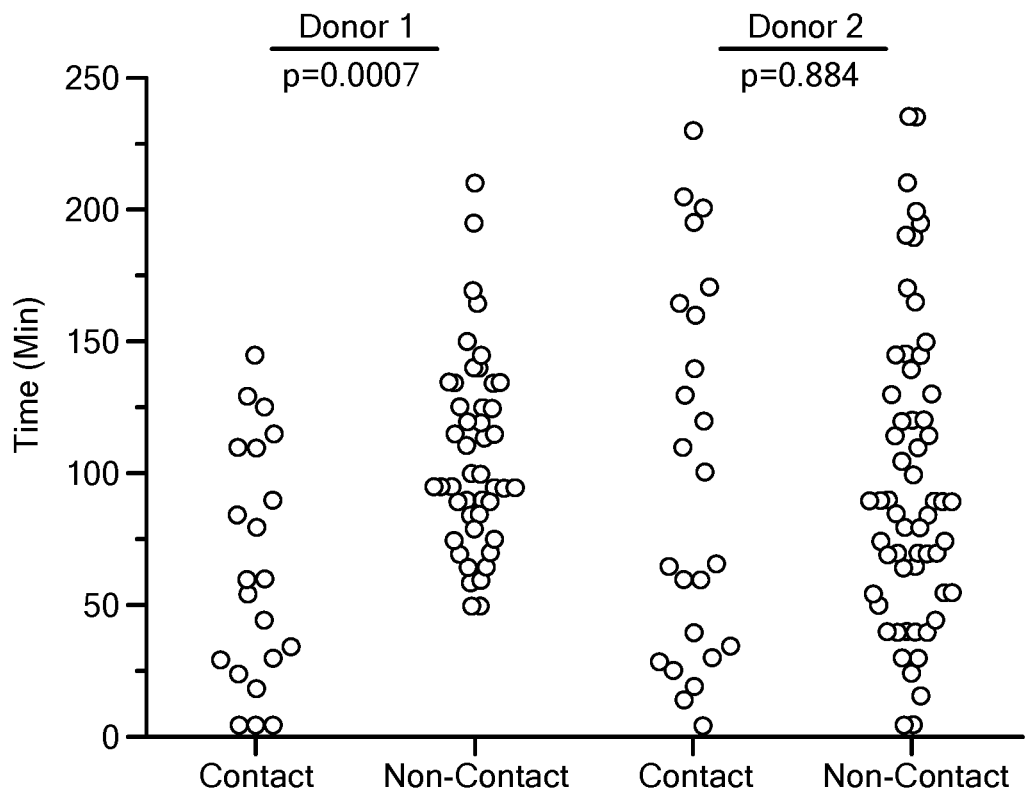
Figure 4E:
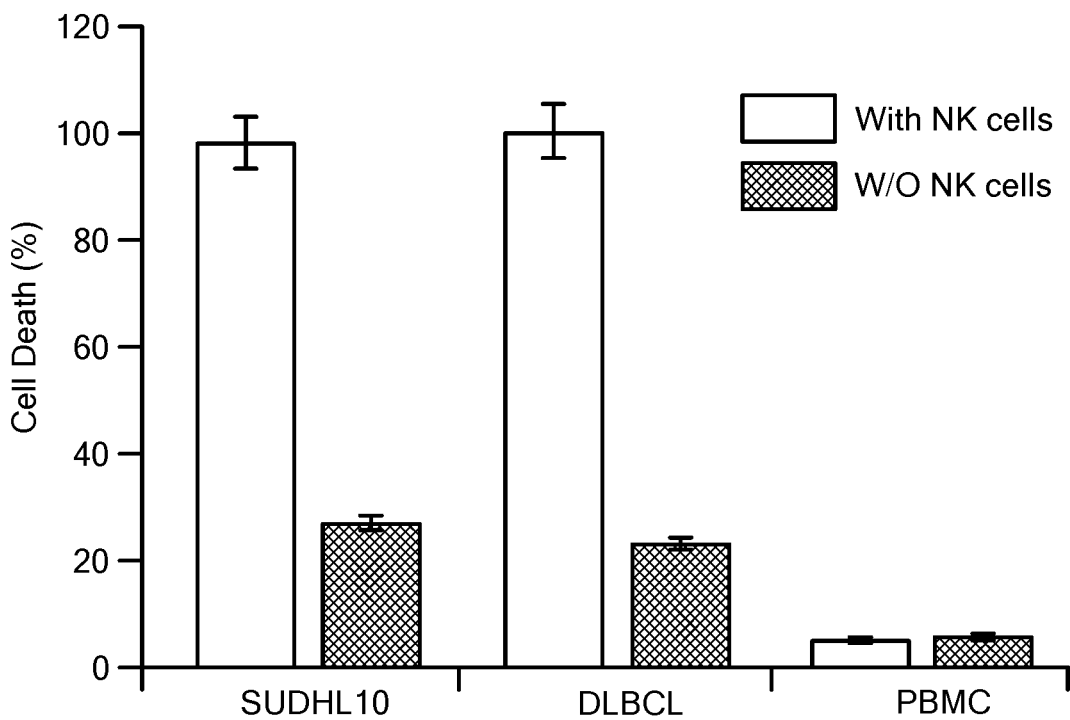

Diffuse Large B cell Lymphoma (DLBCL) cell line SUDHL10 was pre-labeled with Calcein AM, an indicator of live cells, and encapsulated with NK cells in microdroplets. As a negative control, non-tumor cells (peripheral blood mononuclear cell, PBMC) were also encapsulated with NK cells in microdroplets. Target cells that receive lytic hit and undergo damage to the cell membrane show an abrupt loss of Calcein AM, quantifiable as decrease in fluorescent intensity, as well as morphological blebbing and membrane rupture (FIG. 4A). Varying E:T ratios in the same experiment allowed us to observe single NK cell making simultaneous contact with multiple targets and sequentially killing them in 1.5 h (FIG. 4B). This NK cell could be functionally classified as a highly active cell. The findings demonstrate significant heterogeneity in contact dynamics and target cell killing by NK cells (FIG. 4D). Target cell death was observed by both contact-dependent as well as contact-independent methods. Contact-independent target cell death appears to be preferential towards cancer cell lines, as the NK cells did not kill PBMCs co-encapsulated in droplets (FIG. 4C), therefore demonstrating the capability of the present microfluidic system to discriminate immune responses to various types of target cells. Successful on-demand delivery of reagents and biological samples to droplets by the merging apparatus was also observed (FIG. 2C). The merging of the droplets was apparent by the change in diameter of the droplets from 122±5.43 µm (mean±standard deviation) to 210±5.89 µm (FIG. 2A.iii). The data suggests merging efficiency of ~80% at the constricted neck merging.

Example 5

Determination of Effector Cell Heterogeneity at Single-Cell Level in Droplets

Figure 3:
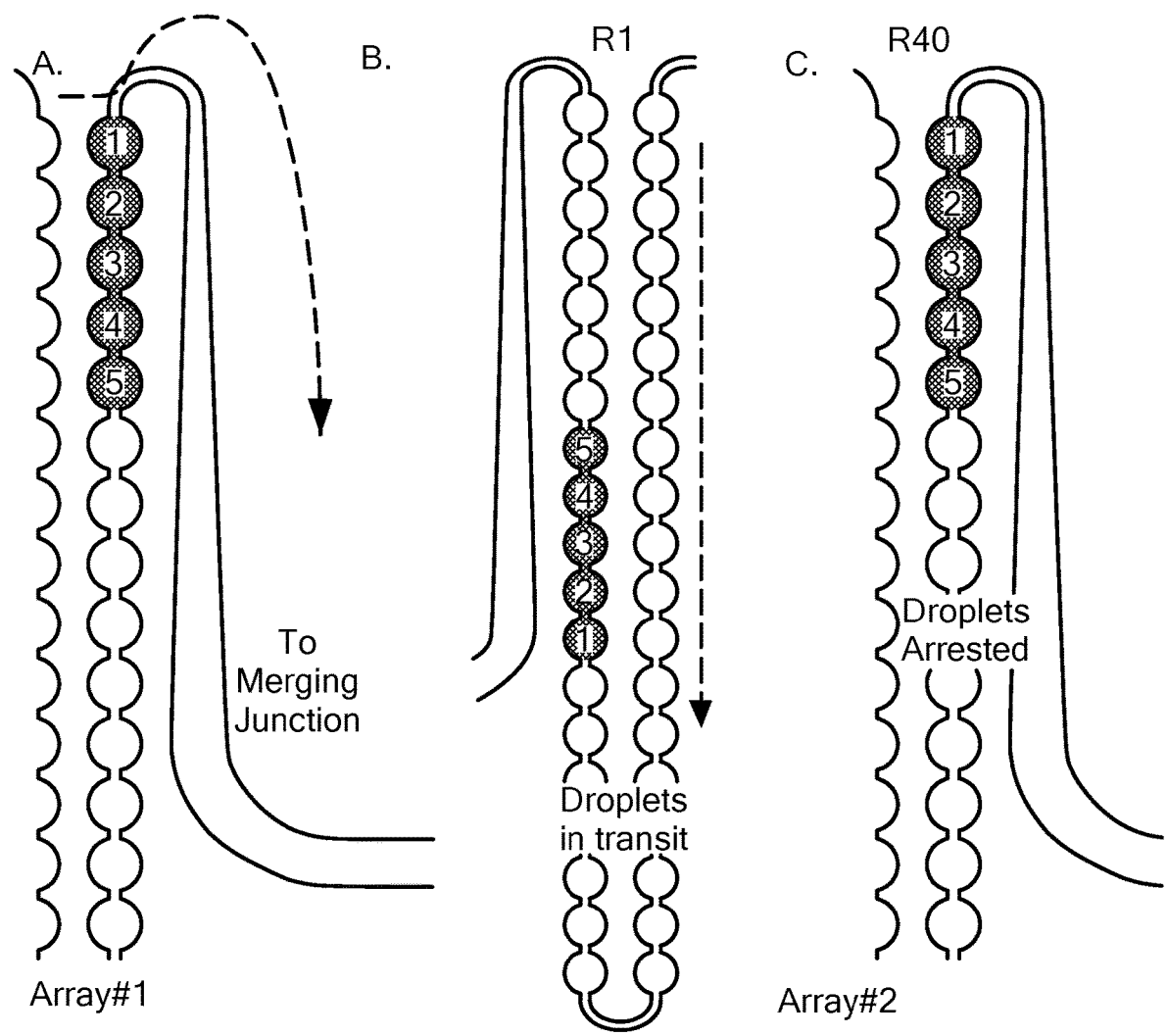
FIG. 3 shows a schematic representation of the two-array design of the microfluidic droplet system.

Primary human NK cells (CD56+ or CD16+), derived from commercial sources (buffy coat) by positive selection (EasySep™ Kits, Stem Cell Tech) according to the manufacturer's protocols, will be co-encapsulated with target Diffuse Large B cell Lymphoma (DLBCL) cell lines representing different NHL subtypes (SUDHL4, SUDHL10) in microfluidic droplets and housed in the first array (FIG. 3, Array #1). These two NK subsets have distinct methods of killing target cells: some of the potential mechanisms involve contact-dependent release of perforin/Granzyme, contact-independent release of cytokines such as IFN-γ or exosomes containing perforin/Fas. NK cells and the target DLBCL cells will be segregated in individual effector (E) and target (T) cell pairs in sub-nanoliter droplets and monitored by automated high-resolution microscopy over 6 hours. Approximately 4000 cell pairs will be monitored; cells will be maintained at 37° C. and 5% $CO_2$ in a stage-top incubator, and imaged at rapid intervals 5 min) using automated Zeiss software. Target cell cytolysis will be assessed by the loss of Calcein AM, a fluorescent indicator of live cells, and by the uptake of propidium iodide. Decrease in fluorescent intensity of Calcein AM due to leakage from the compromised cell membrane will be quantified over the experimental time period to evaluate lytic hits. Heterogeneity in NK cell-mediated cytotoxicity will be assessed by quantifying the proportion of target cells killed by contact-dependent vs. contact-independent means. In addition, different subpopulations of NK cells ("serial killers" versus low/non-cytotoxic subsets) will be identified.

Example 6. Formation of Discrete Microscale Agarose Matrix

Following interaction of NK and target cells in media in droplets, liquid-phase droplets will be converted into solid-phase agarose beads. The primary droplets, containing NK and target cells, will be driven toward the merging junction by fluid pressure, where the "pinched neck" constriction decreases droplet velocity significantly, forcing prolonged contact with the 2% agarose stream, leading to droplet merging. The merged droplets, containing two cell types in 1% agarose, will then be trapped in the second docking array (FIG. 2B.iv). The outflow of the droplets from Array #1 (FIG. 3) will enter the second docking array (Array #2) sequentially. The temperature of the filled droplet array will be lowered to 4° C. to promote the sol-gel transition of the ultra-low temperature gelling agarose (Type IX-A, Sigma Aldrich). This will result in embedding the cell pairs in discrete agarose matrices in the docking array.

Example 7. Detection of Protein Expression in Droplet Agarose Matrices

Following gelation of the agarose droplets in the array, the oil phase will be removed by washing the stable agarose beads and treating chemically with acetone, isopropyl alcohol, and/or deionized water. Care will be taken to avoid denaturing intracellular proteins and RNAs. The embedded cells will then be fixed and permeabilized, and subsequently incubated with fluorescently labeled antibodies (to distinguish $CD56^{bright/dim}$ and $CD16^{+/-}$ NK cells and CD20, MICA/B, and/or ICAM1 for target cells).

Example 8. Microdroplet-Based Multiplexed Detection of Protein and RNA Expression and Functional Analysis of Cell Activity Effector (NK cells) and target cells will be encapsulated at a ratio of 1:4 in droplets to promote serial killing. Dynamic interaction and functional cytotoxicity will be monitored in the formed droplets, which will subsequently be merged with agarose droplets. Following fixation and permeabilization, immunostaining will be conducted with perforin and granzyme antibodies to allow infering cytotoxic protein levels in NK cells. Location of the cytotoxic molecules, i.e., cytolytic granules, late endosome, and interface of immunological synapse, will be determined by counter-staining with LysoTracker red, Rab7 and cell surface marker antibodies, respectively. These steps will be followed by single-molecule mRNA FISH to assess perforin and granzyme B mRNA levels in the same cells and correlate it to protein levels. Hybridization will be conducted at 37° C. in 10% formamide and 2× saline-sodium citrate (SSC). ViewRNA® Cell Plus Assay probes (Affymetrix eBioscience) having 20 base pairs will be used. RNA expression will be detected by microscopy using 60× objectives with large numerical aperture. As control, NK cells will be treated with cycloheximide, which prevents protein synthesis, during the process of serial killing at varying time points (30 min-6 h). The effect of IL-2/IL-15 cytokines, which activate NK cells and therefore could restore mRNA and protein levels to enhance their cytotoxicity, will also be determined. Lastly, secretion of cytokines such an IFN-γ will be analyzed to indicate NK cell activation.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

The invention claimed is:
1. A method for detecting nucleic acid expression in a single cell, the method comprising the steps of:
 (a) providing a fluorescence imaging microscope and a microfluidic device capable of forming an array of aqueous microdroplets in oil, the device comprising first and second translucent microdroplet array chambers;

(b) preparing a plurality of first aqueous microdroplets in an oil phase using the microfluidic device, each microdroplet comprising one or more cells, and transporting the plurality of aqueous microdroplets into the first microdroplet array chamber;

(c) analyzing an activity of the one or more cells of each first microdroplet in the array chamber using the fluorescence imaging microscope for a period of time; wherein the activity comprises a change over said period of time of one or more of the following: an effect of a therapeutic agent on a cell, cell shape or size, a cell-cell interaction, a cell-cell communication, translation of a protein, an immunoregulation, secretion of a factor from a cell, an activity of an immune cell, an antigen specificity of a cell, a cell interaction with a polymer scaffold or with an extracellular matrix component, cell activation, cell viability, cell growth, cell proliferation, cell development, and cell motility;

(d) transporting the first microdroplets out of the array chamber and through a microdroplet merging device, where the first microdroplets are individually merged with second microdroplets containing a biocompatible matrix precursor to form a plurality of third microdroplets;

(e) transporting the third microdroplets into the second microdroplet array chamber and causing the matrix precursor to form a biocompatible matrix embedding one or more cells within each third microdroplet;

(f) fixing and permeabilizing the cells embedded within the plurality of third microdroplets;

(g) incubating the third microdroplets with one or more fluorescently-labeled oligonucleotide probes, and analyzing expression of a gene and/or protein related to the change of the activity of step (c);

(h) detecting the oligonucleotide probes in individual cells within the third microdroplets in the second microdroplet array chamber using the fluorescence imaging microscope; and (i) determining the expression of one or more nucleic acids in individual cells based on the detected oligonucleotide probes.

2. The method of claim 1, wherein the nucleic acid is mRNA.

3. The method of claim 1, wherein the biocompatible matrix is selected from the group consisting of agarose, alginate, and hydrophilic polymers.

4. The method of claim 1, wherein the cells are non-adherent cells.

5. The method of claim 1, wherein the method comprises two or more types of cells.

6. The method of claim 5, wherein at least one type of cell is an immune cell and at least one type of cell is a tumor cell.

7. The method of claim 1, wherein one or more additional reagents are added to the aqueous microdroplets after their formation using a droplet merging junction.

8. The method of claim 7, wherein at least one of the additional reagents is an antitumor agent.

9. The method of claim 1, wherein the method comprises simultaneous analysis of at least 1000 aqueous microdroplets.

10. The method of claim 1, wherein the method comprises simultaneous analysis of at least 4000 aqueous microdroplets.

11. The method of claim 1, wherein aqueous microdroplets are sorted and routed to a selected fluidic pathway, chamber, or off-device location, according to an optical signal detected in the aqueous microdroplets.

12. The method of claim 1, wherein steps (a) to (h) are performed in 10 hours or less.

13. The method of claim 1, wherein step (f) further comprises a dehydration step.

14. The method of claim 1, further comprising detection of a protein species by antibody staining.

15. The method of claim 1, wherein the activity analyzed in step (c) is cytotoxicity.

16. The method of claim 1, wherein quantitative analysis of gene expression in two or more cells is obtained following analysis of interaction of the two or more cells within a microdroplet in step (c).

17. The method of claim 16, wherein the method comprises simultaneous analysis of at least 1000 groups of two or more interacting cells.

18. The method of claim 16, wherein the method comprises simultaneous analysis of at least 4000 groups of two or more interacting cells.

19. The method of claim 16, wherein one of the two or more interacting cells is an immune cell and another of the two or more interacting cells is a tumor cell.

20. The method of claim 19, wherein the immune cell is an NK cell.

21. The method of claim 19, wherein immune cells and tumor cells are present in a ratio from 1:1 to 1:10.

22. A microfluidic device for detecting nucleic acid expression in a single cell, the device comprising:

a first inlet for an oil and a second inlet for a first aqueous suspension of cells, wherein the first inlet is fluidically connected to a first microchannel and the second inlet fluidically connected to a second microchannel;

a nozzle formed by a T-shaped intersection of the first and second microchannels, the nozzle capable of producing a plurality of first aqueous microdroplets suspended in the oil, the first aqueous microdroplets comprising the cells;

a first microdroplet array chamber having a first end fluidically connected to the nozzle and operative to capture and display each of the first microdroplets in a first sequential order in the first microdroplet array chamber, a second end fluidically connected to an inlet end of a droplet merging junction comprising an expansion region upstream and a constricted neck downstream fluidically connected to an outlet end, and a translucent window configured to allow imaging of first microdroplets in the first microdroplet array chamber;

a second microdroplet array chamber, fluidically connected to the outlet end of the droplet merging junction;

a third inlet for an aqueous reagent solution, the third inlet connected to the inlet end of the droplet merging junction and configured to provide one or more reagents in a plurality of second aqueous microdroplets;

wherein the droplet merging junction is configured to merge the first and second microdroplets, one-by-one, resulting in formation of a plurality of third microdroplets, wherein each third microdroplet is formed by the merger of a single first microdroplet with a single second microdroplet;

wherein the device is configured to transport the third microdroplets from the outlet end of the droplet merging junction to the second microdroplet array chamber and to capture and display the third microdroplets in a second sequential order in the second microdroplet array chamber; and wherein the second sequential order of third microdroplets in the second microdroplet array chamber replicates a first sequential order of first microdroplets in the first microdroplet array chamber.

23. A system for detecting nucleic acid expression in a single cell, the system comprising:
the microfluidic device of claim 22;
a fluorescence imaging microscope; and
optionally, an imaging device for forming images of cells in microdroplets in the microfluidic device using the fluorescence imaging microscope; and
optionally, a computer for recording and/or analyzing the images of cells.

24. The method of claim 1, wherein the activity analyzed in step (c) is an activity of a cancer-associated immune cell, immunoregulation by a cytotoxic lymphocyte, an activity of an NK cell, antigen specificity of a T cell, an interaction between a T cell and a target cell, serial interactions between a cell pair, synapse formation between an NK cell and a target cell, an interaction between an effector cell and an antigen-presenting cell, an interaction between an effector cell and a target cell.

* * * * *